US011369666B2

(12) United States Patent
Morris et al.

(10) Patent No.: US 11,369,666 B2
(45) Date of Patent: Jun. 28, 2022

(54) TREATMENT OF DISEASES INVOLVING MUCIN

(71) Applicant: NewSouth Innovations Pty Limited, University of New South Wales (AU)

(72) Inventors: David L. Morris, Lugarno (AU); Roger Aston, Nedlands (AU); Javed Akhter, Nedlands (AU); Krishna Pillai, Nedlands (AU)

(73) Assignee: NewSouth Innovations Pty Limited, New South Wales (AU)

( * ) Notice: Subject to any disclaimer, the term of this patent is extended or adjusted under 35 U.S.C. 154(b) by 557 days.

(21) Appl. No.: 14/649,518

(22) PCT Filed: Dec. 17, 2013

(86) PCT No.: PCT/AU2013/001474
§ 371 (c)(1),
(2) Date: Jun. 3, 2015

(87) PCT Pub. No.: WO2014/094041
PCT Pub. Date: Jun. 26, 2014

(65) Prior Publication Data
US 2015/0343035 A1 Dec. 3, 2015

(30) Foreign Application Priority Data
Dec. 17, 2012 (AU) ............... 2012905519

(51) Int. Cl.
| | | |
|---|---|---|
| *A61K 38/48* | (2006.01) | |
| *A61K 31/198* | (2006.01) | |
| *A61K 33/24* | (2019.01) | |
| *A61K 33/243* | (2019.01) | |
| *A61K 38/17* | (2006.01) | |
| *A61K 36/88* | (2006.01) | |
| *A61K 45/06* | (2006.01) | |

(52) U.S. Cl.
CPC ........ *A61K 38/4873* (2013.01); *A61K 31/198* (2013.01); *A61K 33/243* (2019.01); *A61K 36/88* (2013.01); *A61K 38/1709* (2013.01); *A61K 45/06* (2013.01); *C12Y 304/22032* (2013.01); *C12Y 304/22033* (2013.01)

(58) Field of Classification Search
CPC .. A61K 38/4873; A61K 31/198; A61K 33/24; A61K 36/88; A61K 38/1709; A61K 45/06; C12Y 304/22032; C12Y 304/22033
See application file for complete search history.

(56) References Cited

U.S. PATENT DOCUMENTS

| 6,517,832 B1 | 2/2003 | Marrongelle et al. |
| 2008/0075710 A1 | 3/2008 | Cornett et al. |
| 2010/0166726 A1 | 7/2010 | Campbell |

FOREIGN PATENT DOCUMENTS

JP 08-337532 A 12/1996

OTHER PUBLICATIONS

Chobotova et al. (Cancer Letters vol. 290, Issue 2, Apr. 28, 2010, pp. 148-156).*
PLATINOL® Prescribing Information of Sep. 2010.*
Zafarullah et al. (Cell. Mol. Life Sci. 60 (2003) 6-20).*
Baratti et al. Annals of Surgical Oncology 15(2):526-534.*
English Translation of DE 4302060 A1 (DE '060), published Jul. 28, 1994.*
Pillai et al. (J Glycobiol 2013, S1-S10 http://dx.doi.org/10.4172/2168-958X.S1-005).*
Borsig et al., titled "Synergistic effects of L- and P-selectin in facilitating tumor metastasis can involve non-mucin ligands and implicate leukocytes as enhancers of metastasis," PNAS Feb. 19, 2002, vol. 90, No. 4, pp. 2193-2198.*
International Search Report corresponding to PCT/AU2013/001474 dated Jan. 24, 2014, 5 pages (also submitted with subject application at filing).
Levenson, Stanley M. M.D. et al., "Chemical Debridement of Burns: Mercaptans," *The Journal of Trauma* (Aug. 1981); 21(8):632-644.
Zheng Fulin et al., *Complete Collection of Practical Clinical Medicine Books*, Anhui Science & Technology Publishing House, 1$^{st}$ edition, Mar. 1998, p. 1336.
Glazer, A. N. and Smith, E. L., "The Sulfur Distribution of Papain," *The Journal of Biological Chemistry*, Jan. 1965, vol. 240, No. 1, p. 201-208.
Maurer, H. R., "Bromelain: biochemistry, pharmacology and medical use," *Cell. Mol. Life Sci.*, 2001, vol. 58, p. 1234-1245.
Bromelain Monograph, *Alternative Medicine Review*, 2010, vol. 15, No. 4, p. 361-368.

* cited by examiner

Primary Examiner — James D. Anderson
Assistant Examiner — William Y Lee
(74) Attorney, Agent, or Firm — Kilpatrick Townsend & Stockton LLP

(57) ABSTRACT

The present invention relates to compositions containing one or more of the compounds contained in bromelain, or salts, solvates or prodrugs thereof, and one or more mucolytic agents, or salts, solvates or prodrugs thereof, for treatment of diseases involving mucin, especially mucin secreting cancers, or diseases involving blood clots (thrombi).

16 Claims, 14 Drawing Sheets

Fig. 3
ACTION OF NAC AND BROMELAIN ON SOFT MUCIN
Fig. 3(a)
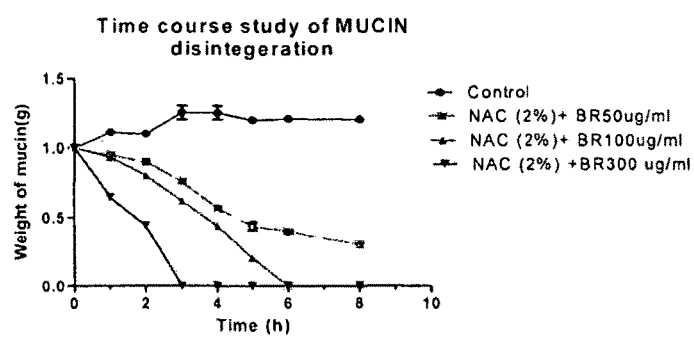
Fig. 3(b)
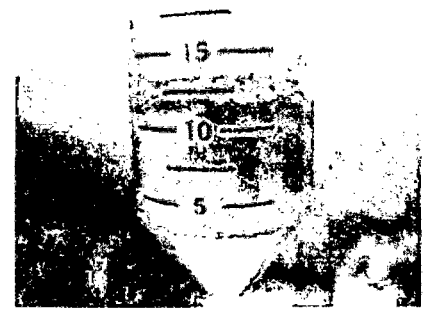
Clear liquid in tube treated with NAC/Br 300 ug/ml

Animal studies (pilot) 48h

Results: Table A. *In vivo* efficacy of Bromelain and N-Acetylcystein (NAC) in nude rats.

| Animal number | Treatment | Frequency | Mucin implanted (g) | Mucin recovered (g) |
|---|---|---|---|---|
| 1 | Bromelain+ NAC | Twice a day | 2.0 | No visible mucin |
| 2 | Bromelain + NAC | Twice a day | 2.0 | 0.2 |
| 3 | Tris buffer | Twice a day | 2.0 | 2.2 |

Fig. 5

RESULTS

| Treatment | Mucin recoverd post treatment |
|---|---|
| Bromelain treatment followed by NAC(5%) (24 +24 h) | |
| Bromelian 50µg/mL followed by NAC | 0.4g |
| Bromelian 100µg/mL followed by NAC | None |
| Bromelian 200µg/mL followed by NAC | Very little slimy fluid |
| Bromelain 300µg/mL followed by NAC | Very little slimy fluid |
| | |
| Bromelain and NAC (5%) mixture | |
| Bromelain 50µg/mL + 5% NAC | None |
| Bromelian 100µg/mL + 5% NAC | None |
| Bromelian 200µg/mL +5% NAC | None |
| Bromelian 300µg/Ml +5% NAC | 0.4g soft mucin traped underneath the organs |
| | |
| Control | 1.2g |

Fig. 6
Fig. 6(a)    Fig. 6(b)    Fig. 6(c)
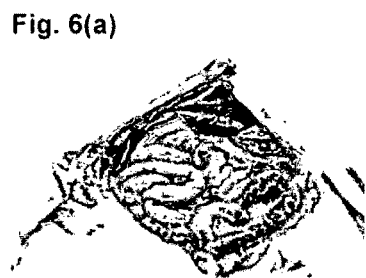  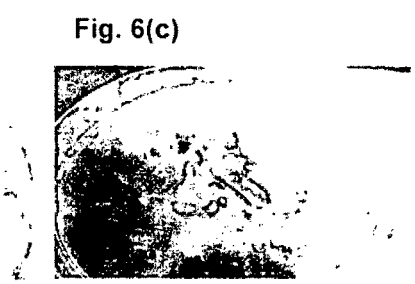
Control rat    Mucin from control    Mucin from 50ug/ml Br
Fig. 6(d)
200ug/ml Br + 5% NAC Fig. 7(a)-(c) Combination of Br and NAC. Cells were treated with NAC and Br simultaneously. After 72 hours incubation, cells were subjected to SRB assay Fig. 8(a)-(c) With a "semi" effective dose of Cisplatin, the addition of Br and NAC produced considerably greater inhibition Fig. 9
Fig. 9(a)
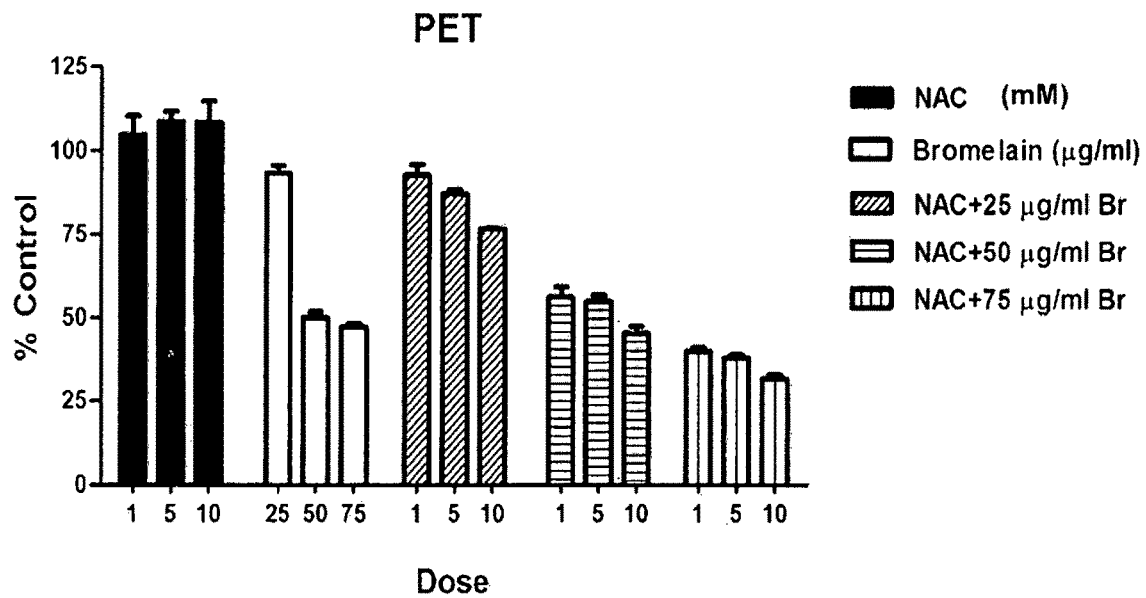
Fig. 9(b)
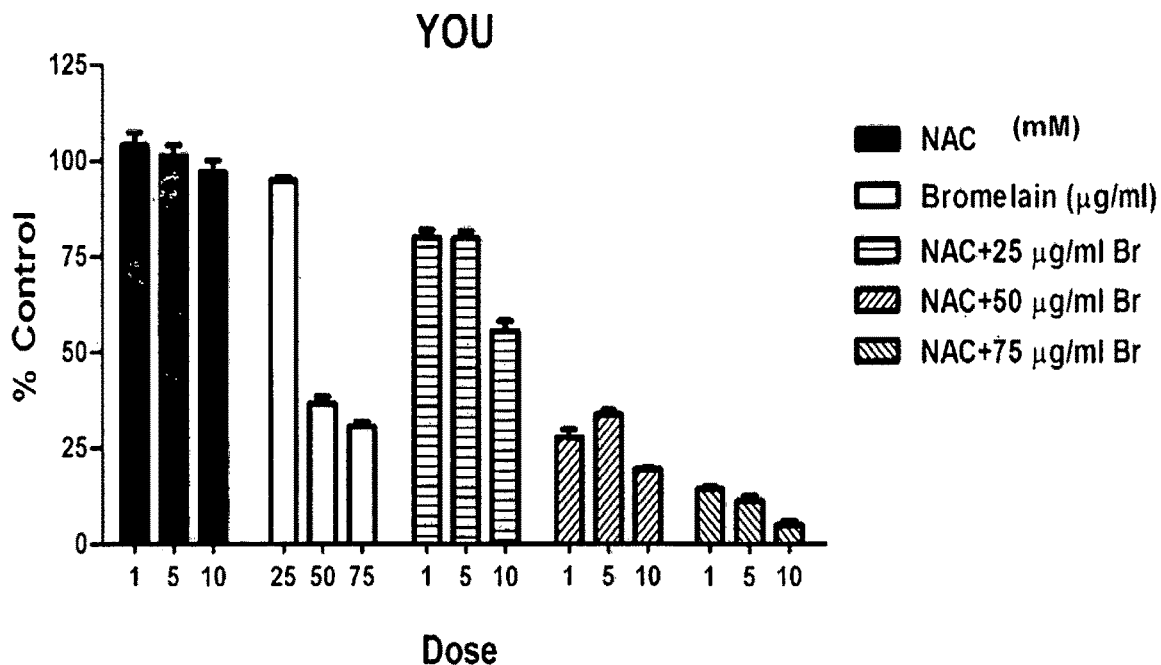

Fig. 10
Fig. 10(a)
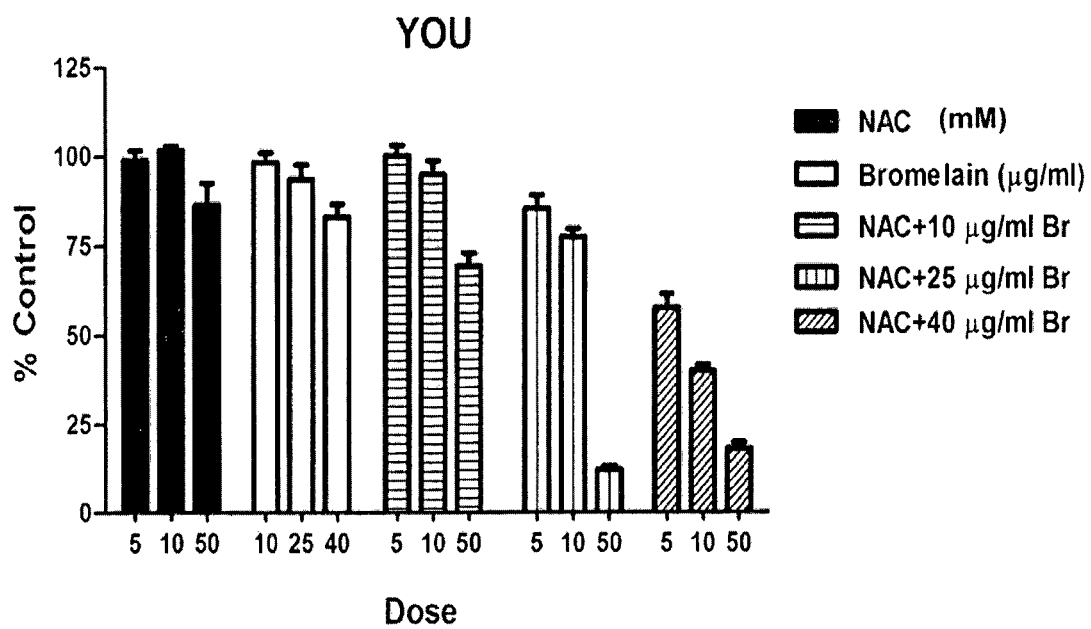
Fig. 10(b)
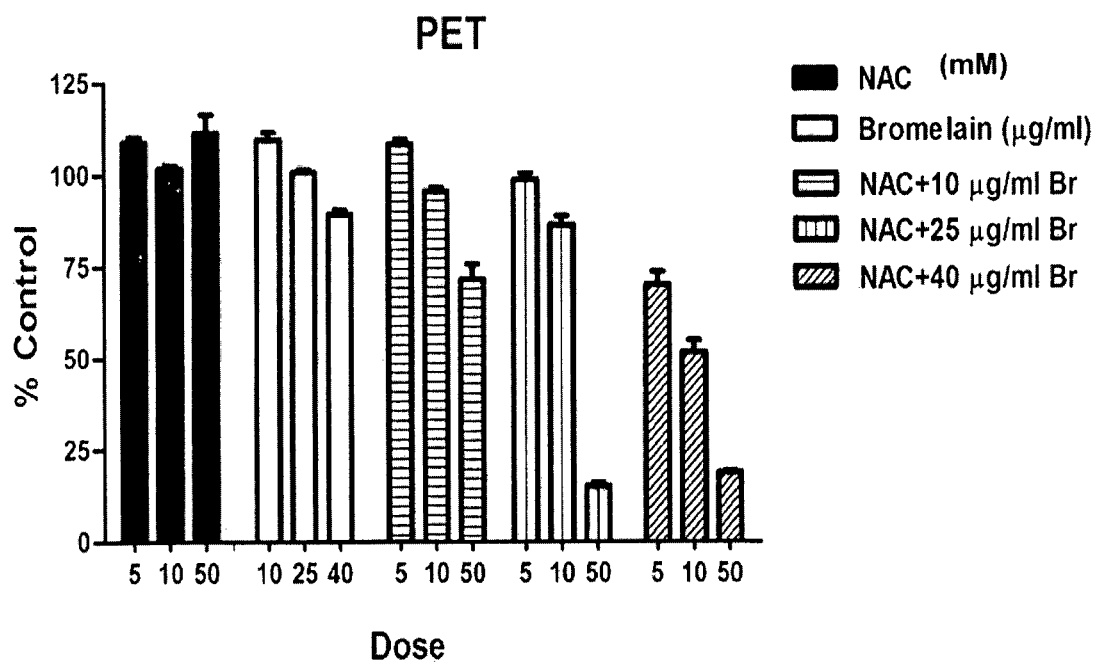

Fig. 11
Fig. 11(a)
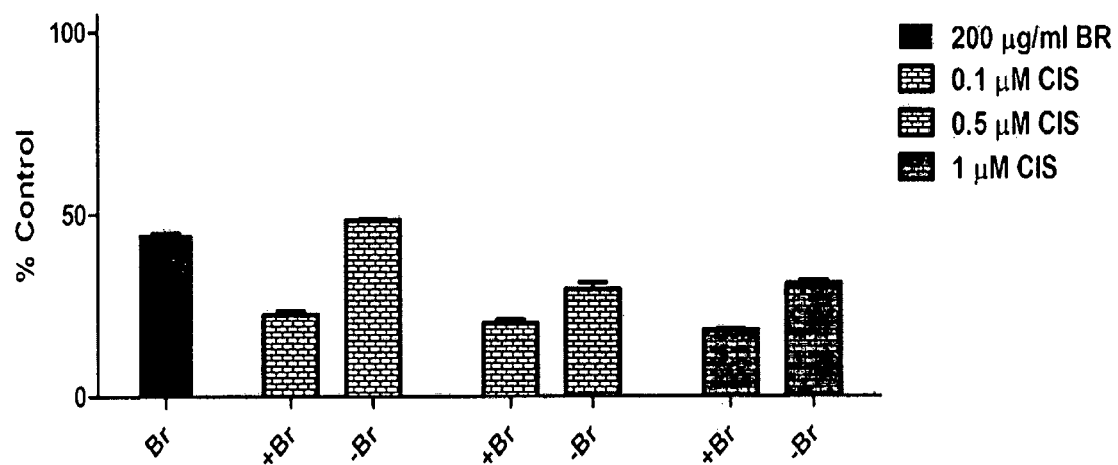
Fig. 11(b)
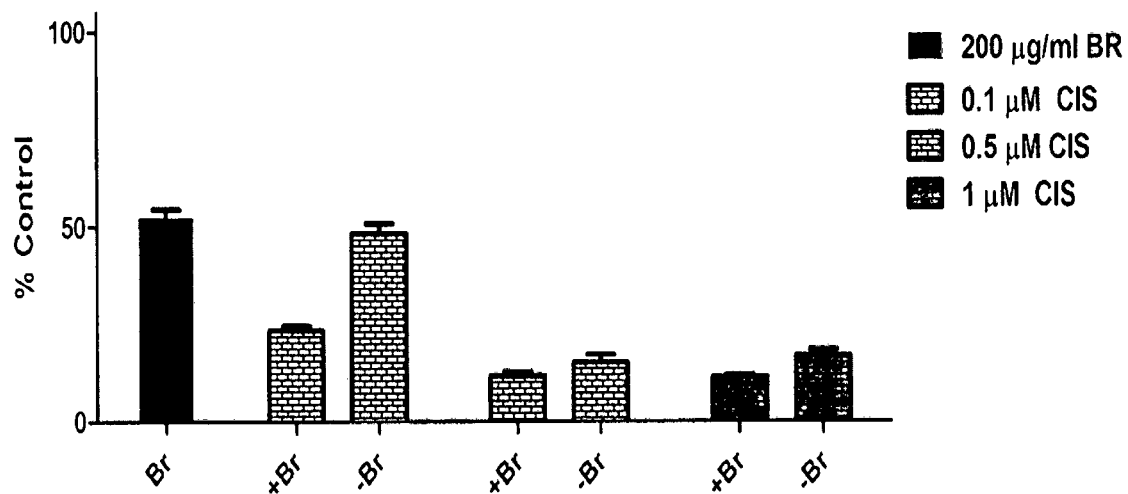

Fig. 12
Fig. 12(a)
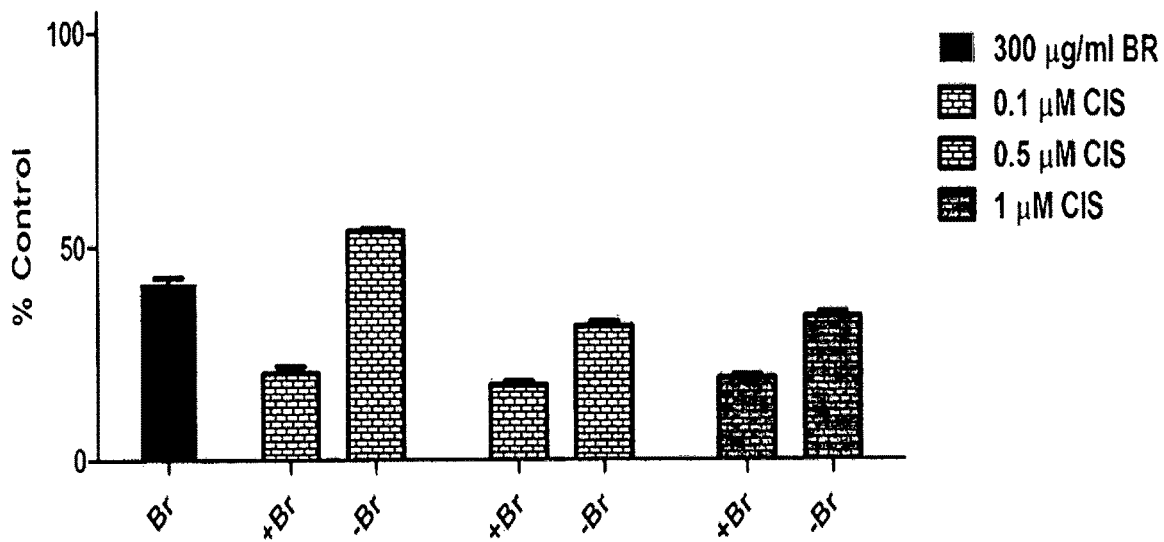
Fig. 12(b)
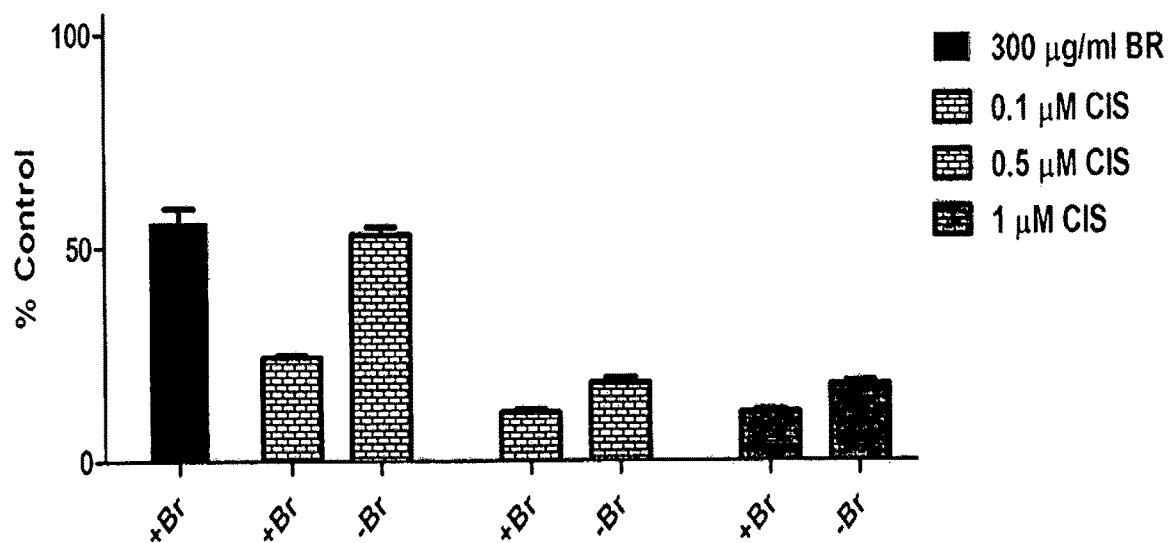

TREATMENT OF DISEASES INVOLVING MUCIN

FIELD

In general, the present invention relates to compositions for the treatment of diseases involving mucin, and specifically for the treatment of mucin-secreting cancers. Additionally, the composition of the present invention relates to compositions for the treatment of diseases involving blood clots (thrombi).

BACKGROUND

Mucins are a family of high molecular weight, heavily glycosylated proteins produced by epithelial tissues including the gastrointestinal tract, lungs, kidneys, ovaries, breast, and pancreas. Under normal physiological conditions, mucin plays a protective role for epithelial tissues. However, mucins can also be involved in disease states (such as cystic fibrosis). The failure to expectorate mucus can lead to diseases including respiratory disease and pancreatic pathology.

A high-level expression of mucin is associated with metastasis and poor clinical outcome in patients diagnosed with cancer. The synthesis of, mucin on the surface of epithelial cells is normally highly regulated, but in tumors there is increased production of mucin partly due to an increased expression of human mucin (MUC1). Mucus expression and composition is altered in cancers of epithelial origin, and mucus production is known to be a negative prognostic factor. The secreted and transmembrane mucins that constitute the mucus barrier are considered to promote tumour progression.

Pseudomyxoma peritonei ("PMP") is a syndrome characterized by the gradual filling of the abdomen with mucin produced by a tumor most commonly arising in the appendix. This filling of the abdomen causes significant discomfort and in severe cases can lead to the death of the patient. Traditionally, repeated debulking operations are performed. However, this has the consequence of increased morbidity and even death.

The formation of blood clots (thrombi) lies at the basis of a number of serious diseases such as myocardial infarction, coronary artery disease, stroke, massive pulmonary embolism and acute limb ischaemia. The likelihood of suffering thrombosis may also be increased in patients who are fitted with a stent.

Anticoagulant drugs (such as heparin and warfarin) may be used to treat thrombosis. However, such anticoagulants only inhibit the formation of thrombi or inhibit the growth of existing thrombi.

There is therefore a need to treat diseases involving mucin and provide better outcomes for patients suffering from diseases involving mucin. In addition, there is a need to treat disorders involving thrombi and provide better outcomes for patients suffering from disorders involving thrombi. It has now surprisingly been found that compositions comprising one or more compounds in bromelain and at least one mucolytic agent are effective in reducing the production of mucin and in aiding the removal of mucin from the body, have a direct inhibitory effect on tumor growth, and can increase the cytotoxicity of chemotherapy drugs.

In addition, it has surprising been found that compositions comprising one or more compounds in bromelain and at least one mucolytic agent are effective in the dissolution of thrombi.

SUMMARY OF INVENTION

According to a first aspect of the present invention, there is provided a composition comprising:
- one or more compounds in bromelain, or a metabolite(s), pharmaceutically acceptable salt(s), solvate(s) or prodrug(s) thereof; and
- at least one mucolytic agent, or a metabolite, pharmaceutically acceptable salt, solvate or prodrug thereof.

Bromelain ("Br") is an extract of the pineapple plant (*Ananas Comosus*), which is believed to comprise various thiol proteases and is known to have proteolytic activity in vitro and in vivo, and antiedematous, anti-inflammatory, antithrombotic and fibrinolytic activities. The active factors in Br are biochemically characterised only in part. Due to its efficacy after oral administration, its safety and lack of undesired side effects, Br has good compliance among patients as a therapeutic drug.

The one or more compounds in Br is also understood to mean all compounds comprised in Br.

A mucolytic agent is an agent which dissolves mucus and is usually used to help relieve respiratory difficulties. Examples of such mucolytic agents include N-acetyl cysteine ("NAC"), nacystelyn, mercapto-ethanesulphonate, carbocysteine, N-acystelyn, erdosteine, dornase alfa, gelsolin, thymosin $\beta_4$, dextran and heparin.

NAC is also an antioxidant and antigenotoxic agent and its safety in high doses for long periods is well established in man, primarily for respiratory disease. Preferably, the mucolytic agent of the present invention is NAC.

The composition according to the first aspect, wherein the combination is a synergistic combination.

According to a second aspect of the present invention, there is provided the composition according to the first aspect of the invention, additionally comprising at least one further biologically active compound, or a metabolite, pharmaceutically acceptable salt, solvate or prodrug thereof.

A chemotherapeutic agent is a pharmacologic agent for use in the treatment of cancer. Examples of such chemotherapeutic agents include actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil (5-FU), gemcitabine, hydroxyurea, idarubicin, imatinib, mechlorethamine, mercaptopurine, methotrexate, mitoxantrone, oxaliplatin, paclitaxel, pemetrexed, teniposide, tioguanine, valrubicin, vinblastine, vincristine, vindesine, vinorelbine and 5FU.

Preferably, the chemotherapeutic agent of the present invention is cisplatin.

The composition according to the second aspect, wherein the combination is a synergistic combination.

According to a third aspect of the present invention, there is provided a combined preparation of one or more compounds in bromelain, at least one mucolytic agent according to the first aspect of the invention, and optionally at least one biologically active compound according to the second aspect of the invention, for simultaneous, separate or sequential use in therapy.

According to a fourth aspect of the present invention, there is provided the composition according to the first or second aspect of the invention for use as a medicament.

According to a fifth aspect of the present invention, there is provided the composition according to the first or second aspect of the invention for the treatment of one or more diseases involving mucin or for the treatment of one or more diseases involving thrombi.

According to a sixth aspect of the present invention, there is provided use of the composition of the first or second aspect of the invention for the manufacture of a medicament for the treatment of one or more diseases involving mucin or for the treatment of one of more diseases involving thrombi.

According to a seventh aspect of the present invention, there is provided a method for the treatment of one or more diseases involving mucin or for the treatment of one or more diseases involving thrombi, the method comprising administering a therapeutically effective amount of the composition of the first or second aspect of the invention to a patient in need thereof.

The composition of the present invention may be used to treat any disease involving mucin, such as cancer, pseudomyxoma peritonei, glue ear, cystic fibrosis, sputum retention, chest infection and mucus associated with biliary/pancreatic stents, and any disease involving thrombi such as haemophilia, myocardial infarction, coronary artery disease, stroke, massive pulmonary embolism and acute limb ischaemia, stent-related thrombosis or haemarthrosis.

In one aspect, the present invention provides a method for the treatment of a mucin-producing cancer or pseudomyxoma peritonei, the method comprising administering a therapeutically effective amount of bromelain and at least one mucolytic agent, or a pharmaceutically acceptable salt or solvate thereof, to a patient in need thereof, wherein the at least one mucolytic agent is a compound of formula (Ia):

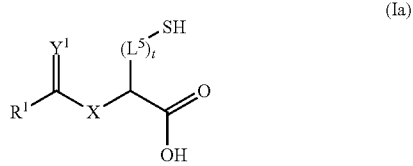

or a pharmaceutically acceptable salt or solvate thereof, wherein $L^5$ is selected from $CR^5R^6$, S, O, CO, $N(R^7)CO$ and $NR^8$; $Y^1$ is selected from O and S; X is selected from $NR^{10}$, O and S; $R^1$ and $R^{10}$ are independently selected from H, alkyl, aryl and heteroaryl; and t is selected from 0 to 20.

In another aspect, the present invention provides a method for the treatment of a mucin-producing cancer or pseudomyxoma peritonei, the method comprising administering a therapeutically effective amount of bromelain in conjunction with a therapeutically effective amount of at least one mucolytic agent, or a pharmaceutically acceptable salt or solvate thereof, to a patient in need thereof, wherein the at least one mucolytic agent is a compound of formula (Ia):

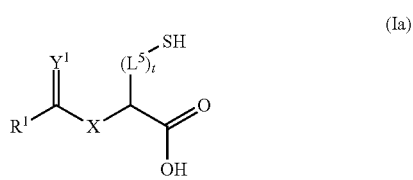

or a pharmaceutically acceptable salt or solvate thereof, wherein $L^5$ is selected from $CR^5R^6$, S, O, CO, $N(R^7)$ CO and $NR^8$; $Y^1$ is selected from O and S; X is selected from $NR^{10}$, O and S; le and are independently selected from H, alkyl, aryl and heteroaryl; and t is selected from 0 to 20.

The composition of the present invention may be used to treat any mucin-secreting cancer, such as lung cancer, breast cancer, colorectal cancer, thyroid cancer, prostate cancer, stomach cancer, pancreatic cancer, cancer of the appendix and ovarian cancer.

The composition of the present invention may be used to treat adenocarcinoma. In particular, the adenocarcinoma may be signet ring cell carcinoma.

According to an eighth aspect of the present invention, there is provided a method for removing mucin from a patient in need thereof using the composition according to the first or second aspect of the invention.

The mucin family includes proteins that contain tandem repeat structures with a high proportion of prolines, threonines and serines (which constitute the PTS domain). Mucins are further defined by extensive glycosylation of the PTS domain through GalNAC O-linkages at the threonine and serine residues as well as other linkages. The human mucin (MUC) family consists of members designated MUC1 to MUC21 that have been sub-classified into secreted and transmembrane forms.

The secreted mucins (for example, MUC2, MUC5AC, MUC5B and MUC6) may form a physical barrier, which as a mucous gel provides protection for epithelial cells that line the respiratory and gastrointestinal tracts and form the ductal surfaces of organs such as the liver, breast, pancreas and kidney.

The transmembrane mucins (for example, MUC1, MUC4, MUC13 and MUC16) have a single membrane-spanning region and contribute to the protective mucous gel through their ectodomains of O-glycosylated tandem repeats that form rod-like structures that extend over 100 nm from the cell surface and beyond the ~10 nm glycocalyx.

MUC1 is aberrantly expressed in a high proportion of carcinomas and certain haematological malignancies making MUC1 overexpression one of the more common alterations in human cancers.

Clones of HT29 colon cancer with different types of mucin secretion have been found to have varying resistance to the common chemotherapy drugs 5FU and methotrexate. Mucin of colonic immuno reactivity conferring resistance to 5FU (mostly MUC 2) and that of gastric reactivity conferring resistance to methotrexate in patients with colorectal carcinoma mucinous histology is associated with poor response rate to chemotherapy and survival. Mucin is known to impede the cytotoxic effect of 5FU against growth of human pancreatic cancer cells. Thus, mucin can act as a cellular barrier limiting chemo therapeutic action. This is further evidenced by the fact that inhibition of mucin O-glycosylation enhances the cytotoxic effects of 5FU against pancreatic cancer cell lines but not against a mucin deficient cell line.

BRIEF DESCRIPTION OF DRAWINGS

FIG. 3 shows the action of the combination of NAC and Br on soft mucin.

FIGS. 4 to 6 show in vivo efficacy of the combination of Br and NAC in nude rats.

FIGS. 8 to 10 show the effects of the combination of NAC and Br on chemotherapy.

FIGS. 11 and 12 show the effect of the combination of NAC and Br on cytotoxic chemotherapy of MUC1 cell lines.

DEFINITIONS

Figure 1:
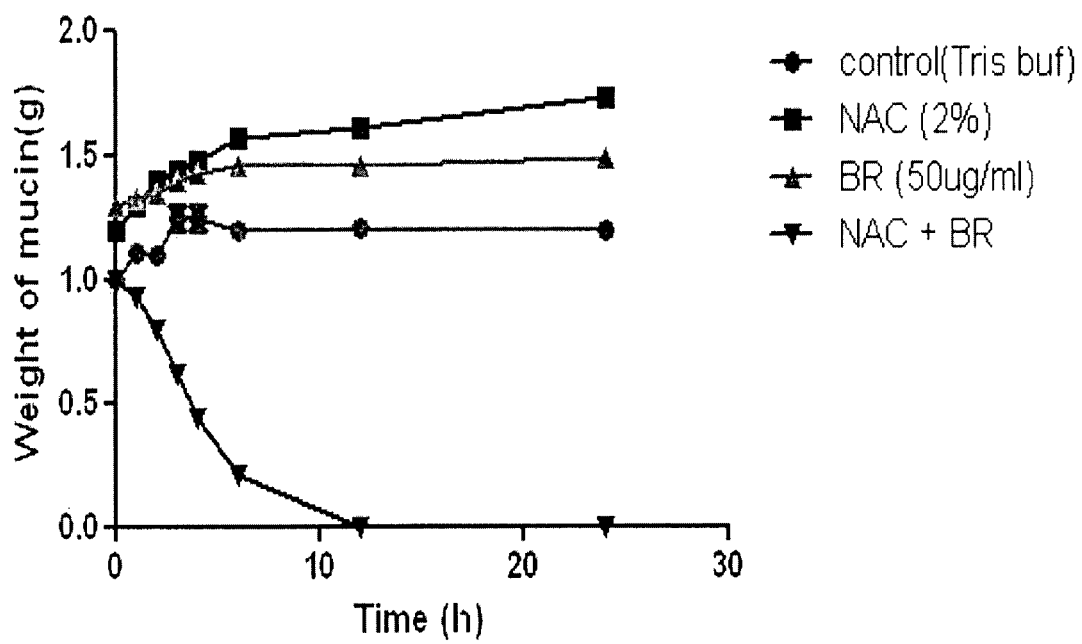
FIG. 1 shows the action of NAC, Br and the combination of NAC and Br on PMP mucin.

"Halogen" means fluorine, chlorine, bromine or iodine, preferably fluorine or chlorine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a straight alkyl chain. "Lower alkyl" means a group having about 1 to about 6 carbon atoms in the chain which may be straight or branched.

"Aryl" by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl. The term "aryl" also includes fused cyclic hydrocarbon rings which are partially aromatic (i.e., one of the fused rings is aromatic and the other is non-aromatic). An exemplary aryl group which is partially aromatic is indanyl.

"Heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups, for use in the invention include carbazolinlyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom:

"Alkyl" or "aryl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH (alkyl),—NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Heteroatom" means an atom selected from N, O, P and S. Where necessary, any undesignated valency is independently selected from H, OH, carbonyl, n-alkyl, aryl or alkoxy.

"p" to "u" may be independently selected from 0 to 20, preferably 0 to 10, more preferably 0 to 6, and most preferably 0 to 4.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Substituted," as in substituted alkyl, means that the substitution can occur at one or more positions and, unless otherwise indicated, that the substituents at each substitution site are independently selected from the specified options, meaning that more than one substituent may be present simultaneously at various sites. Preferably, each substituent has one or more secondary substituents as defined above. Preferably, the secondary substituents are not further substituted.

It is understood that each of the compounds comprised in the composition of the present invention may also relate to a metabolite, pharmaceutically acceptable salt, solvate or prodrug thereof.

"Metabolites" of the compounds of the invention refer to the intermediates and products of metabolism.

"Pharmaceutically acceptable salt" refers to conventional acid-addition salts or base-addition salts that retain the biological effectiveness and properties of the mucolytic agent(s) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457, which is incorporated herein by reference.

"Pharmaceutically acceptable" such as pharmaceutically acceptable carrier, excipient, etc., means pharmacologically acceptable and substantially non-toxic to the subject to which the particular compound is administered.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield the compound of the invention, or a metabolite, pharmaceutically acceptable salt or solvate thereof. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula (I) or (Ia) may contain asymmetric or chiral centres, and, therefore, exist in different stereoisomeric forms. It is intended that all stereoisomeric forms of the compounds of formula (I) or (Ia) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The use of the terms "salt", "solvate", or "prodrug" and the like, is intended to equally apply to the salt, solvate and prodrug of enantiomers, stereoisomers, rotamers, tautomers, positional isomers, racemates or prodrugs of the inventive compounds.

The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation. As used in this application, the singular form "a", "an" and "the" include plural references unless the context clearly dictates otherwise.

As used herein, the term "comprising" means "including." Variations of the word "comprising", such as "comprise" and "comprises," have correspondingly varied meanings. Thus, for example, a pharmaceutical composition "comprising" a compound of formula (I) or (Ia) may consist exclusively of that compound or may include one or more additional components (e.g. a pharmaceutically acceptable carrier, excipient and/or diluent).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

Compositions, Medicaments and Kits

The present invention provides pharmaceutical compositions, medicaments and kits of the present invention and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions, for example water or water-propylene glycol solutions for parenteral injection or intraperitoneal administration or injection, or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxylpropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the composition or medicament.

Composition and medicaments of the present invention may be in a form suitable for administration by injection (e.g. for parenteral administration including intraperitoneal, subcutaneous, intramuscular, or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin, such as almond, corn, arachis, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions and medicaments of the present invention may be administered in the form of a liposome. Suitable methods to form liposomes are known in the art, and in relation to this specific reference is made to Prescott, (Ed), (1976), "Methods in Cell Biology", Volume XIV, Academic Press, New York, N.Y. p. 33 et seq., which is incorporated herein by reference.

Supplementary active ingredients such as adjuvants or biological response modifiers can also be incorporated into compositions and medicaments of the present invention.

Any suitable adjuvant may be included in compositions and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Preferably, the composition of the present invention is delivered by oral, intravenous or intraperitoneal administration when treating mucin-secreting cancers.

Preferably, the composition of the present invention is delivered by intraperitoneal injection when treating PSP.

Preferably, the composition of the present invention is delivered by injection at the site of the thrombus when treating thrombi.

Another aspect of this invention is a kit comprising a therapeutically effective amount of each of a mucolytic agent, one or more compounds in bromelain, optionally one or more biologically active compounds, and a pharmaceutically acceptable carrier, vehicle or diluent.

Another aspect of this invention is a kit comprising a therapeutically effective amount of each of a mucolytic agent, one or more compounds in bromelain, optionally one or more biologically active compounds, and at least one chemotherapeutic agent, wherein the amount of the two or more ingredients results in desired therapeutic effect.

Kits of the present invention may comprise components to assist in performing the methods of the present invention such as, for example, administration device(s), buffer(s), and/or diluent(s). The kits may include containers for housing the various components and instructions for using the kit components in the methods of the present invention.

In certain embodiments, the kits may be combined kits.

In other embodiments, the kits may be fragmented kits.

Dosages and Routes of Administration

The agents, compositions and medicaments can be administered to a recipient by standard routes, including, but not limited to, parenteral (e.g. intraperitoneal, intravenous, intraspinal, subcutaneous or intramuscular), oral, topical, or mucosal routes (e.g. intranasal). In some embodiments, they may be administered to a recipient in isolation or in combination with other additional therapeutic agent(s). In such embodiments the administration may be simultaneous or sequential.

In general, the agents, compositions and medicaments can be administered in a manner compatible with the route of administration and physical characteristics of the recipient (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the agent, composition or medicament is being used as single agent or adjuvant therapy, the progression (i.e. pathological state) of a disease or condition being treated, and other factors readily apparent to those of ordinary skill in the art.

Various general considerations when determining an appropriate dosage of the agents, compositions and medicaments are described, for example, in Gennaro et al. (Eds), (1990), "Remington's Pharmaceutical Sciences", Mack Publishing Co., Easton, Pa., USA; and Gilman et al., (Eds), (1990), "Goodman And Gilman's: The Pharmacological Bases of Therapeutics", Pergamon Press.

In general, an agent, composition or medicament of the present invention may be administered to a patient in an amount of from about 50 micrograms to about 5 mg of active component(s). Dosage in an amount of from about 50 micrograms to about 500 micrograms is especially preferred. Generally, an effective dosage is expected to be in the range of about 0.0001 mg to about 1000 mg of active component(s) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; or about 5.0 mg to about 15 mg per kg body weight per 24 hours.

Typically, in treatment applications, the treatment may be for the duration of the disease state or condition. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

In many instances (e.g. preventative applications), it may be desirable to have several or multiple administrations of an agent, composition or medicament of the present invention which may, for example, be administered 1, 2, 3, 4, 5, 6, 7, 8, 9, 10, or more times. The administrations may be from about one to about twelve week intervals, and in certain embodiments from about one to about four week intervals. Periodic re-administration is also contemplated.

It will also be apparent to one of ordinary skill in the art that the optimal course of administration can be ascertained using conventional course of treatment determination tests.

Where two or more entities (e.g. agents or medicaments) are administered to a subject "in conjunction", they may be administered in a single composition at the same time, or in separate compositions at the same time, or in separate compositions separated in time.

Certain embodiments of the present invention involve administration of the agents, compositions or medicaments in multiple separate doses. Accordingly, the methods for prophylactic and therapeutic treatment described herein encompass the administration of multiple separated doses to a subject, for example, over a defined period of time. Accordingly, in some embodiments the methods include administering a priming dose, which may be followed by a booster dose. The booster may be for the purpose of re-vaccination. In various embodiments, the agent, composition or medicament is administered at least once, twice, three times or more.

The agents, compositions and medicaments may generally be administered in an effective amount to achieve an intended purpose. More specifically, they may be administered in a therapeutically effective amount which means an amount effective to prevent development of, or to alleviate the existing symptoms of, a target disease or condition. Determination of effective amounts is well within the capability of persons of ordinary skill in the art. For example, a therapeutically effective dose of the agents, compositions and medicaments can be estimated initially from cell culture assays. For example, a dose can be formulated in animal models to achieve a circulating concentration range that includes the $IC_{50}$ as determined in cell culture. Such information can be used to more accurately determine useful doses in humans and other mammalian subjects.

A therapeutically effective dose refers to that amount of the agent, composition or medicament to prevent development of symptoms, ameliorate symptoms and/or prolong the survival of the subject under treatment. Toxicity and therapeutic efficacy of the agents, compositions and medicaments can be determined by standard pharmaceutical assays in cell cultures, and/or experimental animals (e.g. by determination of the $LD_{50}$ (the dose lethal to 50% of the population) and the $ED_{50}$ (the dose therapeutically effective in 50% of the population)). The dose ratio between toxic and therapeutic effects is the therapeutic index which can be expressed as the ratio between $LD_{50}$ and $ED_{50}$. Agents, compositions and medicaments which exhibit high therapeutic indices are preferred. The data obtained from such cell culture assays and/or animal studies may be used to formulate a range of dosage for use in humans or other mammals. The dosage of such compounds lies preferably within a range of circulating concentrations that include the $ED_{50}$ with little or no toxicity. The dosage may vary within this range depending upon the dosage form employed and the administration route utilised. The exact formulation, route of administration and dosage can be selected without difficulty by an individual physician in view of the subject's condition (see, for example, Fingl at al., (1975), in "*The Pharmacological Basis of Therapeutics*", Ch. 1 p. 1, which is incorporated herein by reference). Dosage amount and interval may be adjusted individually to provide plasma levels of the active agent sufficient to achieve and maintain the desired therapeutic effect/s and/or a minimal effective concentration (MEC). Dosages necessary to achieve the MEC will depend on the route of administration and other individual characteristics. Bioassays and/or HPLC assays may be used to determine plasma concentrations.

Dosage intervals may also be determined using MEC value. In general, the agents, compositions and medicaments may be administered using a regimen which maintains plasma levels above the MEC for between about 10%-90% of the time, preferably between 30%-90% and more preferably between about 50%-90%. In embodiments where local administration or selective uptake is utilised, the effective local concentration of the drug may not be related to plasma concentration.

A preferred dosage is about 500-50,000 mg/kg of body weight/day of a mucolytic agent, or a metabolite, pharmaceutically acceptable salt, solvate or prodrug of said agent. A preferred dosage when administered into the intraperitoneal cavity or into the tumour itself is about 2000 mg/kg of body weight/day, and an especially preferred dosage is about 2500 mg/kg of body weight/day of a mucolytic agent, or a metabolite, pharmaceutically acceptable salt, solvate or prodrug of said agent. A preferred dosage when administered orally is about 10,000 mg/kg of body weight/day of a mucolytic agent, or a metabolite, pharmaceutically acceptable salt, solvate or prodrug of said agent.

A preferred dosage when administered into the intraperitoneal cavity or into the tumour itself is about 10-50 mg/kg of body weight/day of the one or more compounds in Br, or a metabolite, pharmaceutically acceptable salt, solvate or prodrug of said compound. A preferred dosage when administered orally is about 500-1000 mg/kg of body weight/day of the one or more compounds in Br, or a metabolite, pharmaceutically acceptable salt, solvate or prodrug of said compound.

A preferred dosage of the biologically active compound, or a metabolite, pharmaceutically acceptable salt, solvate or prodrug of said compound is in accordance with the recommended dosage range as indicated in MIMS (the publication "The Monthly Index of Medical Specialties").

The compounds of this invention may also be useful in combination (administered together or sequentially) with one or more of anti-cancer treatments such as radiation therapy, and/or one or more chemotherapeutic agents such as cytostatic agents, cytotoxic agents (such as for example, but not limited to, DNA interactive agents (such as cisplatin or doxorubicin); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); antimetabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4~[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifamib (Zamestra® or R115777 from Janssen Pharmaceuticals), L778.123 (a famesyl protein transferase inhibitor from Merck & Company, Whitehouse Station, N.J.), BMS 214662 (a famesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, Cytoxan, and gemcitabine.

Subjects

Prophylactic and therapeutic methods of the present invention may be applied to any suitable subject. In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

Summary

It has surprisingly been found that the combination of one or more compounds in bromelain and at least one mucolytic agent may be used in the treatment of mucin-producing tumors, in which mucin is secreted from the cell and is present on the surface, and in which either an intracellular globule of mucin is present or a transmembrane mucin is present (the signet cell variety).

The combination of the present invention may be used to treat signet cell cancers of any tumor type such as breast, colorectal, stomach, pancreatic, appendix, ovary and others to directly inhibit tumor growth or facilitate other treatments, and to treat mucin-secreting tumors and tumors which have MUC1, MUC2 or other trans-membrane receptors to directly inhibit tumor growth or facilitate other treatments.

The combination of the present invention:
  significantly increases the effect and cytotoxicity of chemotherapy agents in mucin-producing cancer cells, and has a direct anti tumor effect and inhibitory effect on cancer cell viability and growth,
  profoundly affects tumor-production of mucin, and
  is highly effective in liquefying tumor mucin.

For patients suffering from PSP, an injection of the composition of the present invention into the peritoneum either together or serially fluidises the mucin, allowing the aspiration or removal of the tissue and resolving or ameliorating the patient's problems.

Other situations in the body where the combination of the present invention can be used for the dissolution of mucus include glue ear, cystic fibrosis, sputum retention, chest infection, biliary/pancreatic stents and other situations where mucin deleteriously affects health.

In addition, the combination of the present invention may be used in the dissolution of thrombi and therefore used in the treatment of diseases involving thrombi. Preferably, the combination of the present invention is administered by injection at the site of the thrombus. By dissolving the thrombi, the disease process may be arrested or complications of the disease may be reduced. For example, when haemophiliacs have a bleed into the knee, the present invention may be used to dissolve the thrombus. In addition, other diseases in which the present invention is useful in the dissolution of thrombi include myocardial infarction, coronary artery disease, stroke, massive pulmonary embolism, acute limb ischaemia and stent-related thrombosis.

The present invention will now be described with reference to specific examples, which should not be construed as in any way limiting.

EXAMPLES

| A. | Pseudomyxoma Peritoneii | Laboratory | Experiment 1 31 Patients |
| | | | Experiment 2 Time Course |
| | | | Experiment 3 Time/Concentration |
| | | Animal | Experiment 1 Pilot |
| | | | Experiment 2 In vivo (timing/dose experiments) |
| B. | Mucin Secreting Cancers | Combination Treatments | MKN 45 HT 29 |
| C. | Effect on Chemotherapy | | |

A. Pseudomyxoma Peritonei

Experiment 1 (Laboratory)

Table 1 shows results from PMP tumor from 31 patients who underwent peritonectomy. Table 1 shows that treatment with either Br and NAC alone was ineffective. Specimens of tumor/mucin were taken from the abdomen and then subjected to treatment in the laboratory with 300 µg/ml Br, 5% NAC, or a mixture of both, for 3 hours at 37° C. The weight of mucin tumor was measured before and after treatment. In 16 patient samples there was complete or >90% disappearance of the tumor when the combination of Br+NAC was used, and in every case there was no (or a very modest) reduction of weight with Br or NAC on their own.

TABLE 1

Breakdown of mucin with improved enzyme formulation

| Patient | Treatment | Residual mucin weight post treatment (g) | | Mucin type |
|---|---|---|---|---|
| P1 | Br | 2.13 | 2.97 | soft |
| | NAC | 1.90 | 1.67 | |
| | Br + NAC | 0.06 | 0.09 | |
| P2 | Br | 1.82 | 1.77 | soft |
| | NAC | 1.39 | 1.53 | |
| | Br + NAC | 0 | 0 | |
| P3 | Br | 1.87 | 2.14 | soft |
| | NAC | 1.80 | 1.83 | |
| | Br + NAC | 0 | 0 | |
| P4 | Br | 1.41 | 1.63 | Semi solid |
| | NAC | 1.28 | 1.53 | |
| | Br + NAC | 0.75 | 0.50 | |
| P5 | Br | 1.78 | 1.44 | Hard |
| | NAC | 1.69 | 1.79 | |
| | Br + NAC | 0.87 | 0.85 | |
| P6 | Br | 2.20 | 2.17 | soft |
| | NAC | 2.13 | 2.08 | |
| | Br + NAC | 0 | 0 | |
| P7 | Br | 2.20 | 2.17 | soft |
| | NAC | 2.13 | 2.08 | |
| | Br + NAC | 0 | 0 | |
| P8 | Br | 1.70 | 1.76 | soft |
| | NAC | 0.95 | 1.61 | |
| | Br + NAC | 0 | 0.09 | |
| P9 | Br | 1.78 | 1.71 | Signet ring carcinoma |
| | NAC | 1.42 | 1.56 | |
| | Br + NAC | 0.71 | 0.63 | |
| P10 | Br | 2.23 | 1.97 | Hard |
| | NAC | 1.82 | 1.73 | |
| | Br + NAC | 1.09 | 0.95 | |
| P11 | Br | 1.62 | 1.34 | soft |
| | NAC | 0.24 | 0.1 | |
| | Br + NAC | 0 | 0 | |

TABLE 1-continued

Breakdown of mucin with improved enzyme formulation

| Patient | Treatment | Residual mucin weight post treatment (g) | | Mucin type |
|---|---|---|---|---|
| P12 | Br | 2.25 | 2.23 | Semi Hard |
|  | NAC | 1.81 | 1.94 |  |
|  | Br + NAC | 0.38 | 0.32 |  |
| P13 | Br | 1.36 | 1.92 | Hard |
|  | NAC | 1.73 | 1.43 |  |
|  | Br + NAC | 1.08 | 0.99 |  |
| P14 | Br | 1.32 | 1.60 | soft |
|  | NAC | 1.60 | 1.57 |  |
|  | Br + NAC | 0.15 | 0.12 |  |
| P15 | Br | 1.86 | 1.87 | soft |
|  | NAC | 1.36 | 1.37 |  |
|  | Br + NAC | 0.03 | 0.04 |  |
| P16 | Br | 1.96 | 2.00 | soft |
|  | NAC | 1.69 | 1.62 |  |
|  | Br + NAC | 0.11 | 0 |  |
| P17 | Br | 1.56 | 1.91 | Scraped mucin from mucoid tissues |
|  | NAC | 2.64 |  |  |
|  | Br + NAC | 0 | 0 |  |
| P18 | Br | 2.39 | 2.61 | soft |
|  | NAC | 2.31 | 2.24 |  |
|  | Br + NAC | 0 | 0 |  |
| P19 | Br | 1.95 | 2.04 | Semi soft Mucin deposits on tissue |
|  | NAC | 1.79 | 1.89 |  |
|  | Br + NAC | 0.1 | 0.5 |  |
| P20 | Br | 2.04 | 3.25 | soft |
|  | NAC | 2.34 | 2.36 |  |
|  | Br + NAC | 0 | 0 |  |
| P21 | Br | 2.63 | 2.62 | soft |
|  | NAC | 2.38 | 1.74 |  |
|  | Br + NAC | 0.20 | 0.02 |  |
| P22 | Br | 1.96 | 2.02 | Adeno-carcinoma |
|  | NAC | 1.74 | 1.64 |  |
|  | Br + NAC | 0.54 | 0.47 |  |
| P23 | Br | 2.23 | Not enough sample | Semi solid |
|  | NAC | 1.76 |  |  |
|  | Br + NAC | 0.45 |  |  |
| P24 | Br | 1.90 | 1.61 | Mucin deposits on tissue |
|  | NAC | 1.64 | 1.46 |  |
|  | Br + NAC | 0.17 | 0.14 |  |
| P25 | Br | 1.33 | 1.64 | Hard |
|  | NAC | 1.49 | 1.37 |  |
|  | Bromellan + NAC | 0.39 | 0.55 |  |
| P26 | Br | 1.43 | 1.30 | Hard |
|  | NAC | 1.23 | 1.26 |  |
|  | Br + NAC | 0.52 | 0.55 |  |
| P27 | Br | 1.76 | 2.54 | soft |
|  | NAC | 1.92 | 2.03 |  |
|  | Br + NAC | 0 | 0 |  |
| P28 | Br | 1.74 | Not enough sample | soft |
|  | NAC | 1.48 |  |  |
|  | Br + NAC | 0 |  |  |
| P29 | Br | 1.80 | Not enough sample | soft |
|  | NAC | 1.21 |  |  |
|  | Br + NAC | 0 |  |  |
| P30 | Br | 1.05 | 1.27 | soft |
|  | NAC | 1.26 | 1.16 |  |
|  | Br + NAC | 0 | 0 |  |
| P31 | Br | 2.06 | 1.74 | Hard |
|  | NAC | 1.56 | 1.84 |  |
|  | Br + NAC | 1.06 |  |  |

Experiment 2 (Laboratory)

FIG. 1 shows the time course for dissolution of human PMP mucin in the laboratory. It was found that while again the control of NAC or Br had no effect, the NAC and Br combination had maximal effect within 12 hours, clearly demonstrating the effect of the combination therapy.

Figure 2:
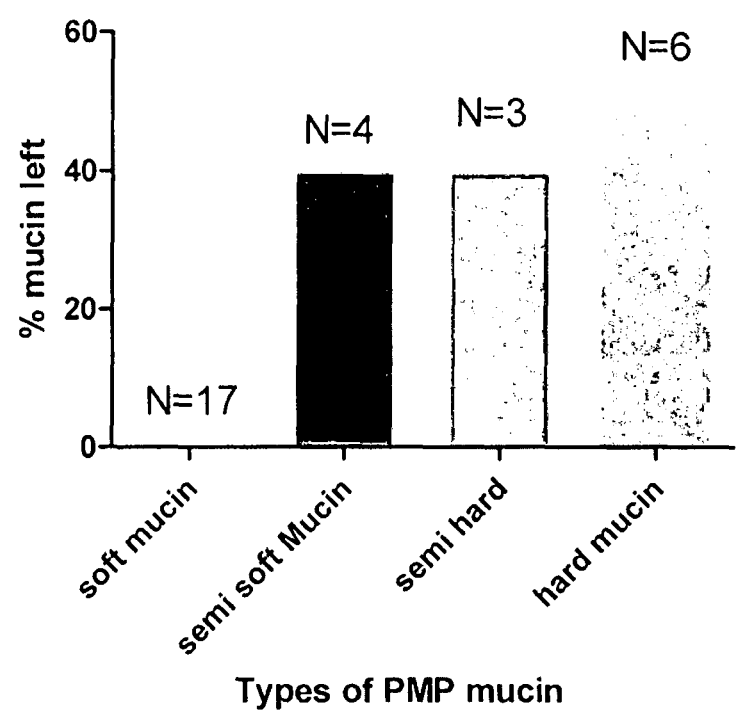
FIG. 2 shows the % weight of mucin remaining after 3 hours following treatment with the combination of NAC and Br.

FIG. 2 shows the relationship between the % of mucin remaining at 3 hours with the combination Br and NAC and the physical appearance of the tumor/jelly. It can be seen that in all the 17 patient samples with soft mucin the mucin dissolved, whereas only 50% reduction in mucin was seen in the 6 patient samples with hard mucin.

Experiment 3 (Laboratory)

Relationship of Time Required for Dissolution to Concentration of Agents

FIG. 3 shows a time course experiment showing complete dissolution of soft mucin by 3 hours with the combination NAC 2% and Br 300 μg/ml compared to 6 hours with the combination NAC 2% and Br 100 μg/ml.

Experiment 1 (Animal Studies)

Figure 4:
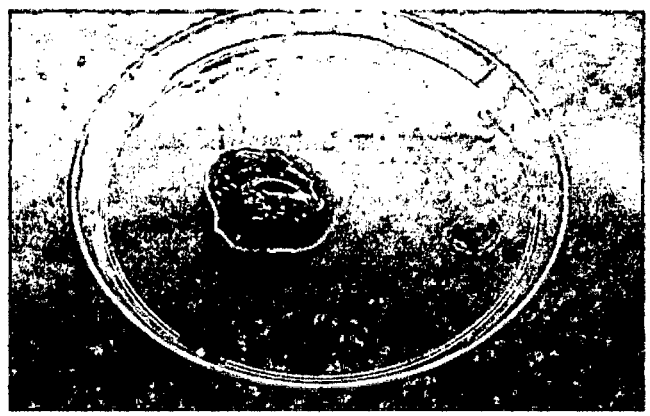

In order to investigate these effects in vivo, 2 grams human PMP mucin were implanted into 3 nude rats and achieved complete or near complete dissolution (see FIG. 4.) in animals treated with Br and NAC and nil dissolution with buffer control.

Experiment 2 (Animal Studies)

These findings were extended with increasing doses of Br in a further 12 rats implanted with 3 grams mucin (see FIG. 5) with little (if any) residual mucin in treated animals and no reduction in controls (see FIG. 6).

No evidence of toxicity or weight loss was seen in the rats over 50 days of treatment.

B. Mucin Secreting Cancers

The significant reduction in tumor weight in a signet ring cancer specimen in the PMP experiments demonstrates that Br and NAC clearly reduces the weight of a cancer with internal mucin (signet ring). The direct effects of the enzyme combination was also studied in cancers as well as PMP.

Figure 7A:
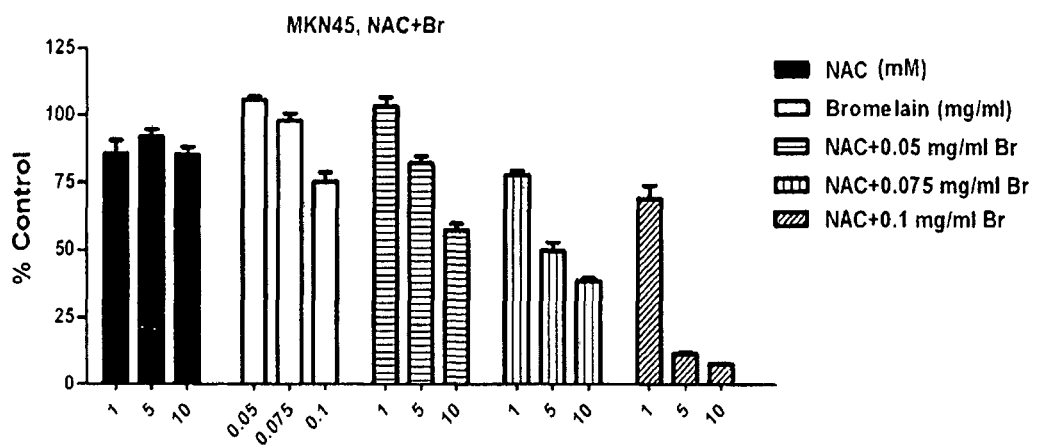
FIG. 7 shows the effect of the combination of NAC and Br on the in vitro growth of various cell lines.

MKN 45 is a human gastric mucin secreting cancer cell line. The effect of NAC, Br and the combination on in vitro growth (SRB assay, 72 hour culture) was studied. FIG. 7(a) shows these results expressed as % of control. NAC and Br individually had no or little effect, whereas combinations of concentrations of NAC and Br which were ineffective produced up to 90% inhibition of growth.

Figure 7B:
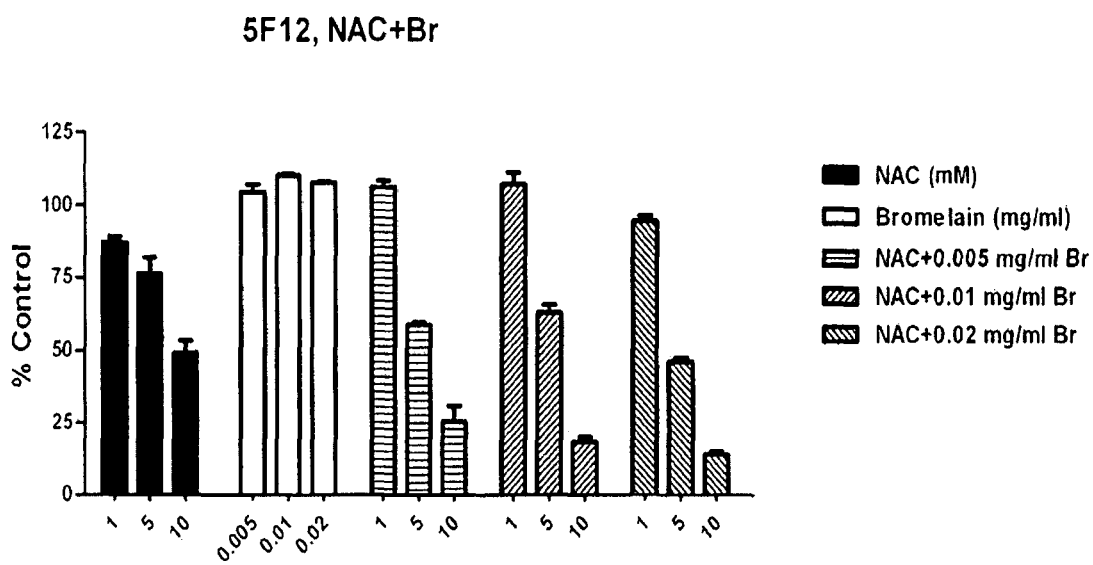

5F12 (FIG. 7b) is a variant of the HT29 colorectal cancer cell line, which secretes gastric type mucin and is resistant to 5FU. Clear synergy between Br and NAC is again seen.

Figure 7C:
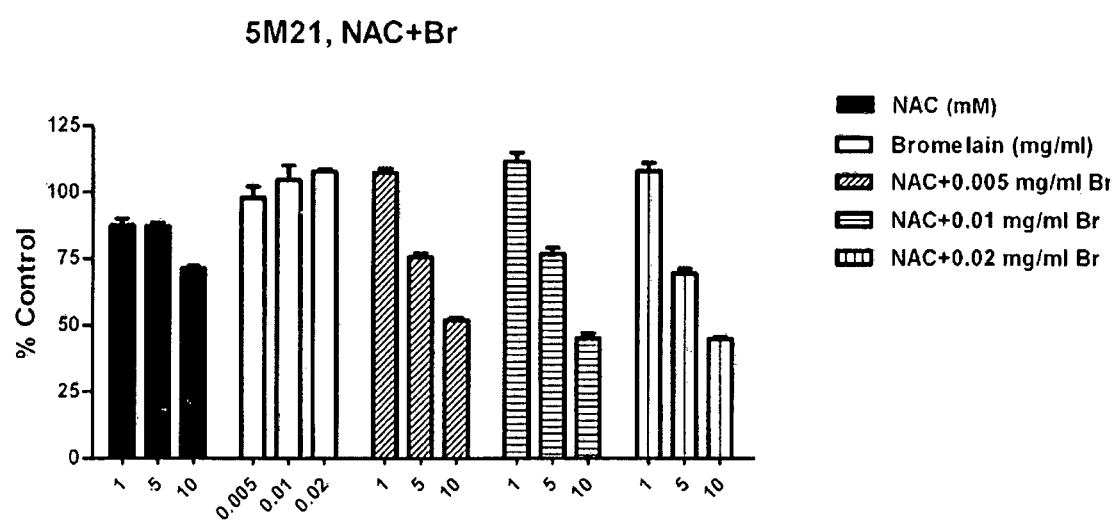

5M21 (FIG. 7c) is a variant of the HT29 cell line, which produces colonic type mucin and is resistant to Methotrexate. Synergy between Br and NAC is again seen.

These findings show that the combination of Br and NAC has highly significant inhibition effects on three cancer cell lines growth, when they had little if any effect on their own.

C. Effects of Br and NAC Combination on Chemotherapy

Figure 8A:
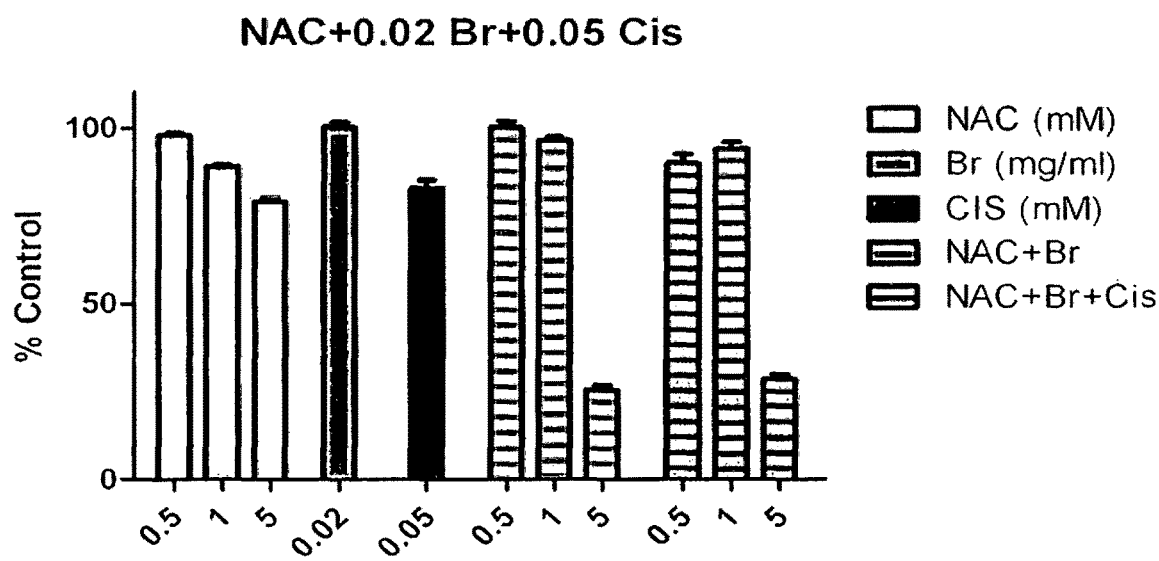
Figure 8B:
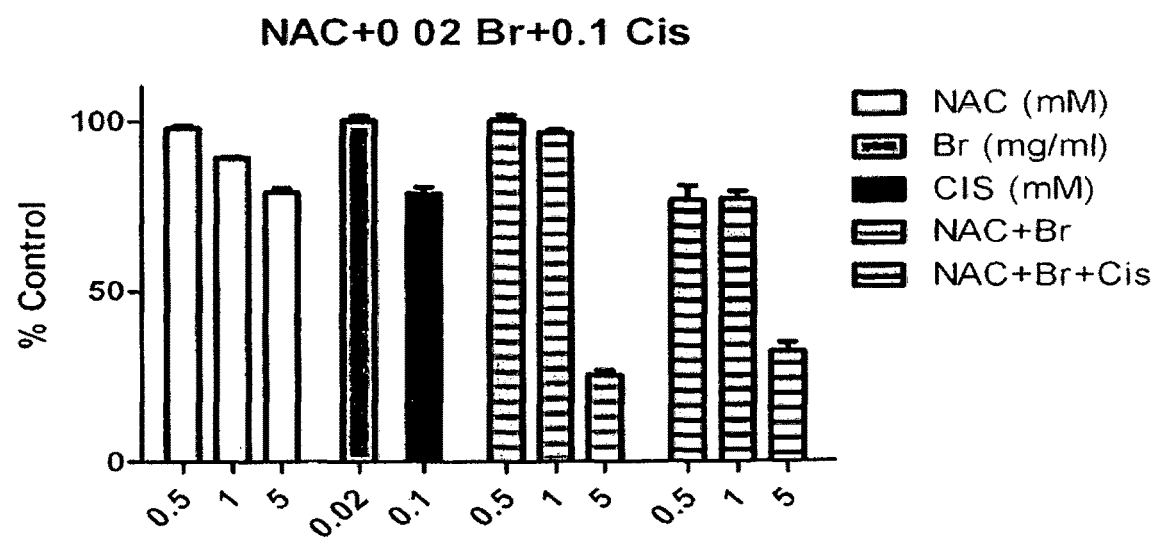
Figure 8C:
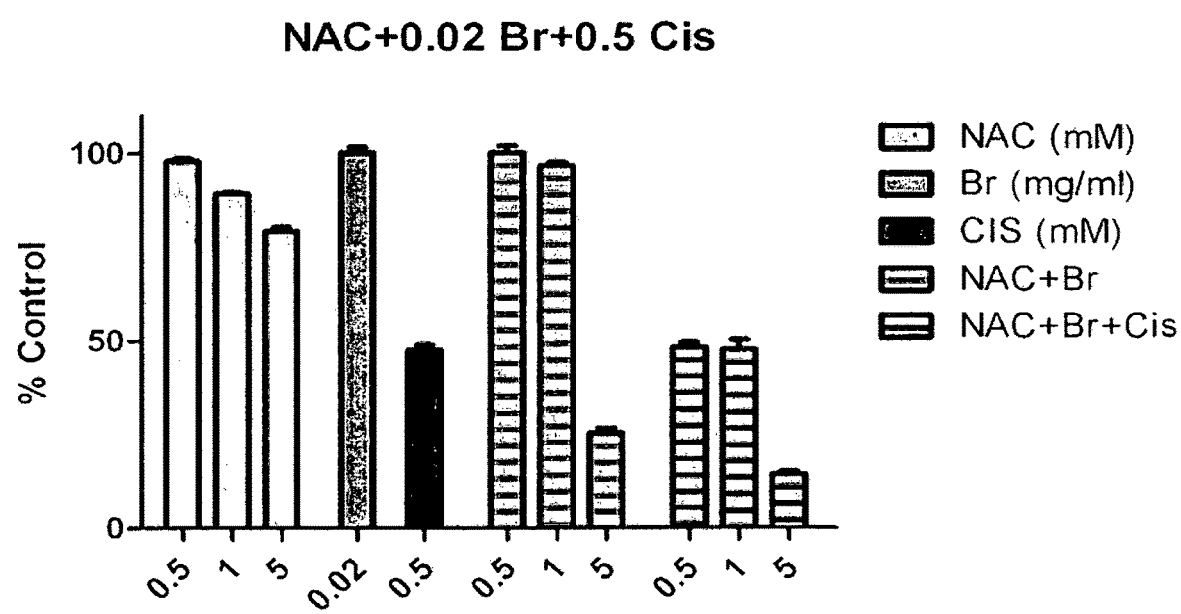

Chemo resistance of mucin secreting cancers is common. The experiments in FIG. 8 again relate to a variant of HT29 (5M21). A combination of Br and NAC was effective, whereas the individual agents were not effective. A combination of Br and NAC and Cisplatin produced more than a doubling of efficacy of Br and NAC, suggesting that Br and NAC may be able to increase the effect of cytotoxic chemotherapy (see FIG. 8c).

MUC 1 (Transmembrane)

MUC 1 is a transmembrane mucin-type glycoprotein with important regulatory function.

The two mesothelioma cell lines PET and YOU (both of which have MUC1) were investigated. These cell lines are different from cancer cells which secrete mucin externally or that have mucin internally in the cell (signet cell). It was found that NAC alone has no action and Br alone produced some growth inhibition (see FIG. 9). The combination of NAC and Br showed improved results, particularly at higher concentrations of NAC (e.g. 50 mM) (and it is noted that 50 mM NAC alone is ineffective) and the combination of NAC and Br 25 μg/ml and the combination NAC and Br 40 μg/ml produced 80-90% inhibition (see FIG. 10).

These findings suggest that MUC1 (and other transmembrane glycoprotein) containing cancers are sensitive to combination therapy with Br and NAC.

Effect of Br and NAC on Cytotoxic Chemotherapy of MUC1 Cells

The combination of Br and NAC with chemotherapy drugs in MUC 1 cell lines was investigated (see FIGS. 11 and 12).

Low doses of Cisplatin were ineffective, and the addition of the combination of Br and NAC doubled the efficacy, suggesting again that Br and NAC significantly increases the effect of cytotoxic chemotherapy in cancer cells with MUC1.

The invention claimed is:

1. A method for the treatment of a mucin-producing cancer or pseudomyxoma peritonei, the method comprising administering a therapeutically effective amount of bromelain and at least one mucolytic agent, or a pharmaceutically acceptable salt or solvate thereof, to a patient in need thereof, wherein the at least one mucolytic agent is a compound of formula (Ia):

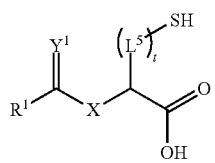

or a pharmaceutically acceptable salt or solvate thereof, wherein $L^5$ is selected from $CR^5R^6$, S, O, CO, $N(R^7)$ CO and $NR^8$; $Y^1$ is selected from O and S; X is selected from $NR^{10}$, O and S; $R^1$, $R^5$, $R^6$, $R^7$, $R^8$ and $R^{10}$ are independently selected from H, alkyl, aryl and heteroaryl; and t is selected from 0 to 20.

2. The method according to claim 1, further comprising administering at least one further biologically active compound or pharmaceutically acceptable salt or solvate thereof.

3. The method according to claim 2, wherein the biologically active compound is selected from any one of chemotherapeutic agent, N-glycosylation inhibitor, silyltransferase inhibitor, multi-drug transport inhibitor, NSAID, antibiotic, and anti-inflammatory agent.

4. The method according to claim 3, wherein the biologically active agent is a chemotherapeutic agent.

5. The method according to claim 4, wherein the chemotherapeutic agent is cisplatin.

6. The method according to claim 1, wherein the cancer is selected from lung cancer, breast cancer, colorectal cancer, thyroid cancer, prostate cancer, stomach cancer, pancreatic cancer, cancer of the appendix and ovarian cancer.

7. The method according to claim 1, wherein the cancer is signet ring cell carcinoma.

8. The method according to claim 1, wherein the mucolytic agent is N-acetylcysteine or a pharmaceutically acceptable salt or solvate thereof.

9. A method for the treatment of a mucin-producing cancer or pseudomyxoma peritonei, the method comprising administering a therapeutically effective amount of bromelain in conjunction with a therapeutically effective amount of at least one mucolytic agent, or a pharmaceutically acceptable salt or solvate thereof, to a patient in need thereof, wherein the at least one mucolytic agent is a compound of formula (Ia):

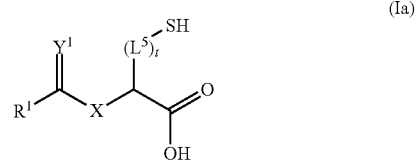

or a pharmaceutically acceptable salt or solvate thereof, wherein $L^5$ is selected from $CR^5R^6$, S, O, CO, $N(R^7)$ CO and $NR^8$; $Y^1$ is selected from O and S; X is selected from $NR^{10}$, O and S; $R^1$, $R^5$, $R^6$, $R^7$, $R^8$ and $R^{10}$ are independently selected from H, alkyl, aryl and heteroaryl;

and t is selected from 0 to 20.

10. The method according to claim 9, further comprising administering at least one further biologically active compound.

11. The method according to claim 10, wherein the biologically active compound is selected from any one of chemotherapeutic agent, N-glycosylation inhibitor, silyltransferase inhibitor, multi-drug transport inhibitor, NSAID, antibiotic, and anti-inflammatory agent.

12. The method according to claim 11, wherein the biologically active agent is a chemotherapeutic agent.

13. The method according to claim 12, wherein the chemotherapeutic agent is cisplatin.

14. The method according to claim 9, wherein the cancer is selected from lung cancer, breast cancer, colorectal cancer, thyroid cancer, prostate cancer, stomach cancer, pancreatic cancer, cancer of the appendix and ovarian cancer.

15. The method according to claim 9, wherein the cancer is signet ring cell carcinoma.

16. The method according to claim 9, wherein the mucolytic agent is N-acetylcysteine or a pharmaceutically acceptable salt or solvate thereof.

* * * * *